United States Patent [19]

Sacceddu et al.

[11] 4,387,163

[45] Jun. 7, 1983

[54] PROCESS FOR PRODUCING THE ENZYME CHOLESTEROL ESTERASE AND FOR HYDROLYZING CHOLESTEROL ESTERS OF FATTY ACIDS BY USING THE ENZYME ITSELF

[75] Inventors: Pasquale Sacceddu, Monterotondo; Vincenza Vitobello, Rome; Paolo Braduzzi, Rome; Nadia Cimini, Rome; Ludwig Degen, Rome, all of Italy

[73] Assignee: E.N.I. Ente Nazionale Idrocarburi, Rome, Italy

[21] Appl. No.: 282,744

[22] Filed: Jul. 13, 1981

[30] Foreign Application Priority Data

Jul. 24, 1980 [IT] Italy ................................ 23656 A/80

[51] Int. Cl.$^3$ .......................... C12N 9/16; C12Q 1/60; C12R 1/025
[52] U.S. Cl. ..................................... 435/197; 435/11; 435/824
[58] Field of Search .................... 435/197, 824, 11, 19

[56] References Cited

U.S. PATENT DOCUMENTS

| 3,925,164 | 12/1975 | Beaucamp et al. | 435/197 |
| 4,011,138 | 3/1977 | Terada et al. | 435/197 |
| 4,042,461 | 8/1977 | Esders et al. | 435/197 |
| 4,052,263 | 10/1977 | Masurekar et al. | 435/197 |

*Primary Examiner*—Lionel M. Shapiro
*Attorney, Agent, or Firm*—George P. Hoare, Jr.

[57] ABSTRACT

The enzyme cholesterol esterase is produced by cultivating a strain of the Achromobacter delicatulus type, isolated from vegetable debris and identified by the symbol NRRL B-12115. Under the described culture conditions, the enzyme is exocellular and therefore does not require extraction from the cells.

In addition, the micro-organism has a duplication time less than that of moulds and Actinomycetes. Cholesterol esters of fatty acids can be hydrolysed by adding them to the culture medium before inoculating the strain.

6 Claims, No Drawings

PROCESS FOR PRODUCING THE ENZYME CHOLESTEROL ESTERASE AND FOR HYDROLYZING CHOLESTEROL ESTERS OF FATTY ACIDS BY USING THE ENZYME ITSELF

This invention relates to a process for producing the enzyme cholesterol esterase (E.C.3.1.1.13) by cultivating a micro-organism of the Achromobacter genus, and to the hydrolysis of cholesterol esters of fatty acids by using the enzyme itself. Cholesterol, an essential component of the human organism, is a basic compound in the constitution of cellular membranes of all tissues, and in the production of numerous hormones. As is well known, the determination of the total cholesterol present in the blood is of great importance in clinical diagnosis, and as it is present in the serum mainly in a form esterified by fatty acids, the enzyme cholesterol esterase is necessary in order to liberate it and hence determine it. Only a few publications describe enzymatic processes for hydrolysing cholesterol esters using enzymes from micro-organisms of the Fusarium, Nocardia, Pseudomonas, Saccharomyces and Streptomyces geni, as the enzyme is obtained from animal tissues.

A process has now been found, and constitutes the subject matter of the present invention, for producing the enzyme cholesterol esterase from a new micro-organism selected by us and pertaining to the Achromobacter genus.

An important advantage of the process according to the present invention is the fact that the enzyme produced by this micro-organism under the culture conditions given hereinafter is exocellular, and it is therefore not necessary to extract it but only concentrate it.

In addition said micro-organism, as a bacterium, has a duplication time which is less than that of moulds and Actinomycetes, and this constitutes a significant working advantage.

This micro-organism, isolated from vegetable debris of the bank of the Tiber, has been classified as *Achromobacter delicatulus* SM-1307, and has been filed at the Northern Regional Center, U.S. Department of Agriculture, Peoria (J 11) under the number NRRL. B.-12115.

Its cultural, morphological and physiological characteristics are given hereinafter.

A-CULTURAL CHARACTERISTICS (1) Solid medium:
 (a) On Nutrient-Agar: colonies of 2 mm diameter after 24 hours of incubation at 30° C., with whole edges which tend to undulate after 7 days of ageing. Convex, off-white colonies of moist, creamy consistency, slightly lucid. No swarming on agarised media.
 (b) On Agar-Gelatin: bright, soft, gelatinous colonies.
(2) Liquid medium:
 (a) On saline broth+yeast extract: cream turbidity with little sediment.
 (b) On peptonised water: good turbidity after 24 hours at 30° C. Sediment and surface film not evident.

B-MORPHOLOGICAL CHARACTERISTICS (1) Gram-negative rod of average length 2 μm.
(2) Positive mobility (hanging droplet observation).
(3) Peritrichous cilia. Densification at the poles not observed.

C-PHYSIOLOGICAL CHARACTERISTICS (1) Optimum growth temperature between 25° and 30° C. Grows well at 20° C. No growth at 42° C.
(2) Does not attack Agar.
(3) Does not produce acid or gas from glucose.
(4) Does not utilise urea.
(5) Does not possess cytochrome-C oxidase.
(6) Reduces nitrates to nitrites.
(7) Is inert in the OX/F test.
(8) Does not produce indole from tryptophan.
(9) Negative methyl red.
(10) Positive catalysis.
(11) Does not produce acid or gas from lactose.
(12) Liquefies gelatin.
(13) Litmus milk: slight acidification after 7 days.

For identification purposes, the procedures used were those indicated in "Methods of detection and identification of bacteria" by B. M. MITRUKA and M. J. BONNER, CRC PRESS INC. 1976, and in "Bergey Manual of Determinative Bacteriology" 7th Edition.

The strain according to the present invention can be cultured under aerobic conditions by submerged culture using agitated fermenters.

A liquid culture medium contains a source of assimilable carbon, a source of nitrogen, and mineral salts. Carbon sources which can be used include amino acids, glucose, oleic acid, linoleic acid, cholesterol esters and sodium acetate. Nitrogen sources which can be used include organic and inorganic nitrogen compounds such as meat extract, yeast extract, peptone, triptane, amino acids, hydrolysed casein, soy flour, nitrates and salts of $NH_4^+$.

A suitable culture medium has for example the following composition:

| | |
|---|---|
| Yeast extract | 1–5 g/l |
| Soy flour | 1–5 g/l |
| $K_2HPO_4$ | Traces up |
| $NaNO_3$, $MgSO_4$ | to 1 g/l |

The pH range for the culture lies between 6 and 8, preferably between 6.8 and 7.2. The temperature range is between 20° C. and 37° C., preferably between 28° C. and 32° C.

The enzyme is produced by adding cholesteryl oleate or natural vegetable oils to the culture medium before inoculation. The hydrolysis of said esters in the culture medium by the cholesterase produced from the *Achromobacter delicatulus* SM 1307 strain constitutes a further subject matter of the present invention.

The induction time can vary from 24 h to 72 h, preferably from 40 h to 48 h.

The culture broth collected during or at the end of the fermentation can be used as such.

Alternatively, the supernatant of the filtered or centrifuged culture broth can be used.

Finally, a further technical and economical improvement can be made by immobilising the enzyme by combination with macromolecular compounds, to form chemical bonds with the matrix, or ionic bonds.

The examples given hereinafter describe further operational methods relating to the present invention, but do not limit it.

EXAMPLE 1

A culture broth was prepared having the following composition:

| | |
|---|---|
| NaNO$_3$ | 2 g/l |
| K$_2$HPO$_4$ | 2 g/l |
| KCl | 0.5 g/l |
| MgSO$_4$.7H$_2$O | 0.5 g/l |
| Yeast extract | 10 g/l |
| Cholesteryl oleate | 5 g/l | by adding the aforesaid compounds to deionised water. The pH of said broth was adjusted to 7.0 with dilute HCl. The medium thus prepared was distributed among 250 ml flasks by adding 50 ml of broth to each flask; they were sterilised at 116° C. for 30 minutes.

They were inoculated with 1 ml of a suspension of the *Achromobacter delicatulus* SM-1307 strain obtained by washing with 10 ml of physiological solution the patina of a culture of 20 ml of Nutrient agar in 200×20 mm tubes, which had been grown for 48 h at 30° C.

The fermentation flasks were incubated under orbital agitation (180–200 r.p.m.) at 30° C.

The culture broths were collected 48 h after inoculation, and tested as such for enzymatic activity. 1 ml of culture broth contained 0.2 enzyme units.

The enzymatic activity was determined in the following manner:

1 ml of culture broth suitably diluted in a 0.1 M phosphate buffer of pH 6.7 was added to 5 ml of a solution of cholesteryl oleate containing 0.3 μmoles/ml in a 0.1 M phosphate buffer of pH 6.7 containing 0.5% of Triton X-100.

The reaction was carried out at 37° C. for 10 minutes in an agitated water bath and was blocked by boiling samples withdrawn from the reaction mixture for 3 minutes.

The concentration of the cholesterol produced by hydrolysing the cholesteryl oleate was determined by the colorimetric method, in which the free cholesterol is oxidised by the cholesterol oxidase to cholest-4-en-3-one with simultaneous production of hydrogen peroxide, which reacts oxidatively with the 4-aminoantipyrin and phenol in the presence of peroxidase to develop a chromogen which has its maximum absorption at 500 mμ.

The optical density of the coloured samples was measured in a DB-GT Beckmann grid spectrophotometer, in which the cuvette had an optical path of 0.1 dm at a wavelength of 500 mμ.

If a unit is defined as that quantity of enzyme which produces 1 μmole of cholesterol per minute under the test conditions stated heretofore, the number of enzyme units pe ml of culture broth is calculated by the following formula:

$$\frac{U}{\text{ml of broth}} = \frac{4 \times 6 \times (E_{10} - E_0)}{5.45 \times 0.1 \times D}$$

in which:

$E_{10}$=optical density of the sample withdrawn after 10 minutes $E_0$=optical density of the sample withdrawn at 0 minutes 5.45=optical density of a cholesterol solution of 1 μmole/ml D=enzyme dilution.

EXAMPLE 2

A culture broth was prepared having the following composition:

| | |
|---|---|
| NaNO$_3$ | 2 g/l |
| K$_2$HPO$_3$ | 2 g/l |
| KCl | 0.5 g/l |
| MgSO$_4$.7H$_2$O | 0.5 g/l |
| Yeast extract | 10 g/l |
| Olive oil | 5 g/l | by adding the aforesaid compounds to deionised water and adjusting to pH 6.7 with hydrochloric acid.

Cultures of the *Achromobacter delicatulus* SM-1307 strain in said broth, and prepared as in example 1, were incubated under orbital agitation (180 r.p.m.) at 30° C.

The culture broths were collected 72 h after inoculation and tested as such for cholesterase activity. 1 ml of culture broth contained 0.4 enzyme units.

EXAMPLE 3

A culture broth was prepared having the composition of example 2.

Cultures of the *Achromobacter delicatulus* SM-1307 strain in said broth, and prepared as in example 1, were incubated under orbital agitation (180 r.p.m.) at 30° C.

The culture broths were collected 72 h after inoculation, centrifuged and the cholesterase of the supernatant was used for determining the total cholesterol present in a sample of human blood serum.

For this purpose, the following reagent was prepared:

| | |
|---|---|
| Sodium cholate | 6 mM |
| Triton X-100 | 15 g |
| Phenol | 7.5 mM |
| 4-aminoantipyrin | 0.5 mM |
| Peroxidase | 16,400 U (Boehringer No. 127361 in catalogue) |
| 0.1 m sodium phosphate buffer pH 7.0 | 1,000 ml. |

The cholesterol was determined in the following manner:

50 μl of human serum and 0.25 ml of culture broth were added to 2.5 ml of reagent.

The reaction took place directly in the glass cuvette, which had an optical path of 1 cm, and the development of the chromogen was followed directly in a DB-GT Beckmann grid spectrophotometer at a wavelength of 500 mμ until complete conversion of the cholesterol present in the serum. Under these conditions, a final optical density of 0.500 was obtained, corresponding to 164 mg of total cholesterol per 100 ml of the human serum sample tested.

We claim:

1. A process for producing the enzyme cholesterol esterase characterised in that the enzyme is produced by cultivating a micro-organism of the *Achromobacter delicatulus* genus identified by the number NRRL B-12115.

2. A process for producing the enzyme cholesterol esterase as claimed in claim 1, characterised in that the micro-organism is cultured within a pH range of between 6 and 8.

3. A process for producing the enzyme cholesterol esterase as claimed in claim 1, characterised in that the micro-organism is cultured within a temperature range of between 20° C. and 37° C.

4. A process for hydrolysing cholesterol esters of fatty acids, consisting of bringing said esters into contact with culture broths of an *Achromobacter delicatulus* NRRL B-12115 strain.

5. A process for producing the enzyme cholesterol esterase as claimed in claim 1, characterized in that the micro-organism is cultured within a pH range of between 6.8 and 7.2.

6. A process for producing the enzyme cholesterol esterase as claimed in claim 1, characterized in that the micro-organism is cultured within a temperature range of between 28° C. and 32° C.

* * * * *